Feb. 3, 1976 W. A. WARRINER Plant Pat. 3,829
ROSE PLANT
Filed Oct. 11, 1974
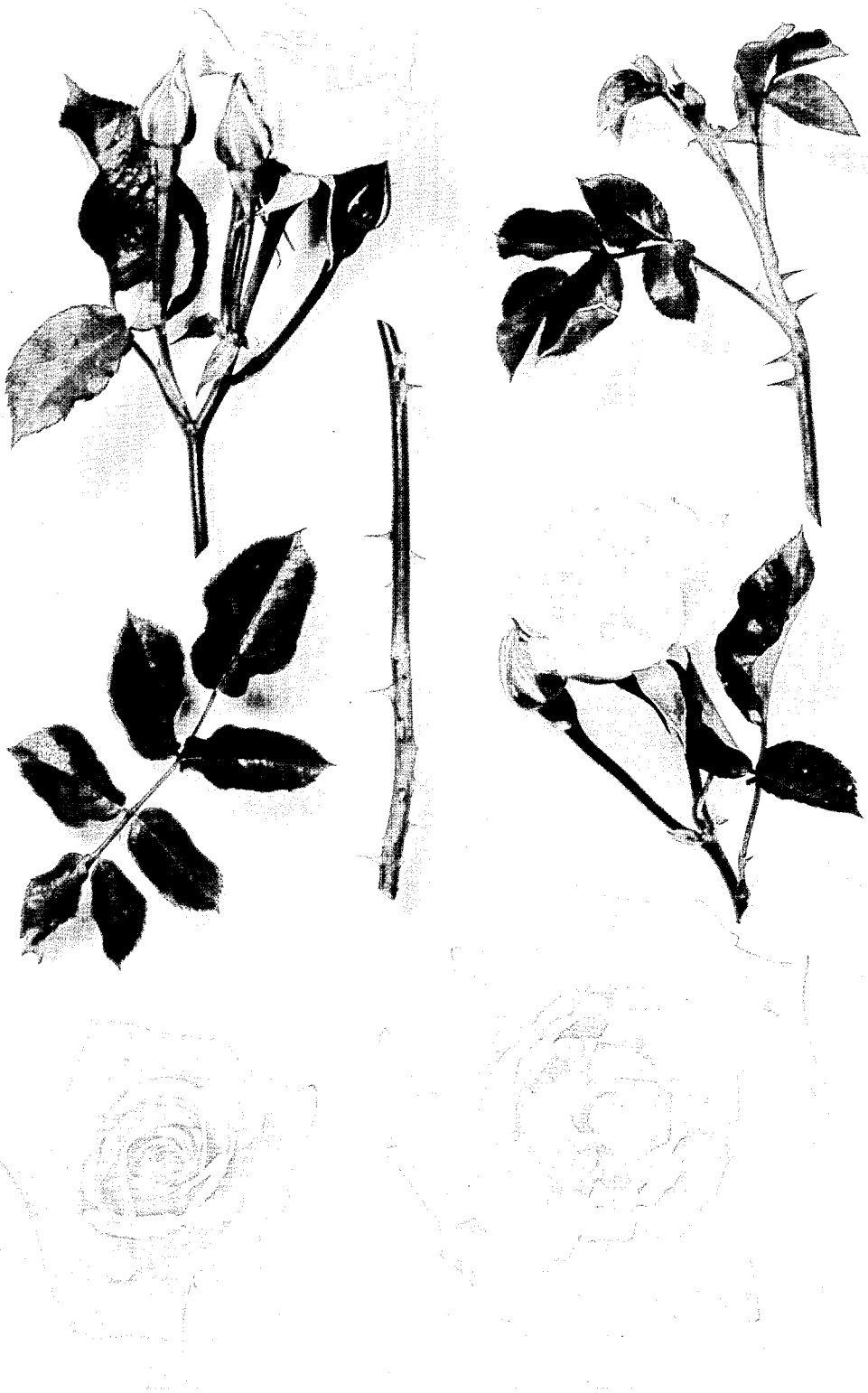

United States Patent

Plant Pat. 3,829

Patented Feb. 3, 1976

3,829

ROSE PLANT

Wililam A. Warriner, Tustin, Calif., assignor to Jackson & Perkins Company, Medford, Oreg.

Filed Oct. 11, 1974, Ser. No. 514,313

Int. Cl. A01h *5/00*

U.S. Cl. Plt.—25 1 Claim

The present invention relates to a new and distinct cultivar of rose plant of the floribunda class, which was originated by me by crossing the cultivar South Seas, U.S. Plant Pat. No. 2,184, with pollen from an unnamed cultivar.

The principal objective of this breeding was to produce a cultivar of the floribunda class bearing large flowers of a color usually referred to as coral or shrimp on a compact, heavily branched plant. This objective was fully achieved, along with other desirable improvements, as evidenced by the following unique combinations of characteristics which are outstanding in the new cultivar and which distinguish it from its parents as well as from all other cultivars of which I am aware:

1. A vigorous, heavily branched plant.
2. Abundantly doubled flowers of a size approximately 2½ inches to 3 inches in diameter.
3. A flower color of Shrimp Red (W).
4. Very little fragrance.

Asexual reproduction of this new cultivar by budding was performed at Wasco, Calif., and shows that the characteristics and distinctions in this description come true to form and are established and transmitted through succeeding propagations.

The accompanying illustration shows typical specimens of the vegetative growth and flowers of the new cultivar in different stages of development and depicted in color as nearly true as it is reasonably possible to make the same in a color illustration of this character.

The following is a detailed description of my new rose variety with color terminology in accordance with *Wilson's Horticultural Color Chart,* except where ordinary dictionary significance of color is indicated.

Parentage: Seedling.
- *Seed Parent.*—South Seas, U.S. Plant Pat. No. 2,184.
- *Pollen Parent.*—Unnamed cultivar.

Classification:
- *Botanic.*—Rosa hybrid.
- *Commercial.*—Floribunda.

FLOWER

Observations were made at Irvine, Calif., in early July.

Blooming habit: Recurrent—continuous.

Bud:
- *Size.*—Approximately 1 inch when petals start to unfurl.
- *Form.*—Pointed ovoid.
- *Color.*—When sepals first divide: near Poppy Red (16/2) with large basal area of Straw Yellow (604) and a suffusion of Straw Yellow (604) along veining. When half bloom; upper side of petals near Shrimp Red (616/1), outer petals suffused with Mandarin Red (17/2). Lower side of petals; near Shrimp Red (616/1) suffused with Straw Yellow (604) and large basal area of Straw Yellow (604).
- *Sepals.*—Color: Outer surface: Scheeles Green (860/3) strongly overlaid with Garnet Brown (00918/3). Inner surface: Scheeles Green (860/3) with moderate amount of white tomentum. Three appendaged sepals lightly appendaged. Two unappendaged sepals hairy edged.
- *Receptacle.*—Color: Scheeles Green (860) with occasional overlay of Garnet Brown (00918/3). Shape: Funnel. Size: Large. Surface: Smooth.
- *Peduncle.*—Length: Long to medium. Surface: Slightly prickly. Color: Garnet Brown (00918). Strength: Stiff, erect.
- *Opening.*—Spiral at first, petal edges roll under.

Bloom:
- *Size.*—Medium. Average open size 2½ inches to 3 inches.
- *Borne.*—Singly and in flat clusters.
- *Stems.*—Medium.
- *Form.*—When first open—high center. Permanence—retains its form to the end.
- *Petalage.*—Number of petals under normal conditions—70.
- *Color.*—Center of flower: Upper side of petals Shrimp Red (616/2). Reverse side of petals: Shrimp Red (616/2). Base of petals: large area of Canary Yellow (2/2) fused irregularly with the Shrimp Red color of balance of petal. General tonality from a distance: Shrimp Red (616/2).
- *Discoloration.*—At end of first day—none. Third day—outer most petals gradually change to a color near Azalea Pink (6R/2).
- *Fragrance.*—Slight.
- *Petals.*—Texture: Thick. Shape: Round. Form: Tips slightly recurved and edges slightly quilled.
- *Arrangement.*—Loosely imbricated.
- *Petaloids in Center.*—Few.
- *Persistence.*—Drop off cleanly.
- *Lastingness.*—On the plant—long. As cut flower—long.

PLANTS

Form: Bush.

Growth: Vigorous, upright, branching.

Foliage: Number of leaflets on normal mid-stem leaves, 5 or 7.
- *Size.*—Medium.
- *Quantity.*—Normal.
- *Color.*—New foliage: near Spinach Green (0960/2) suffused with Garnet Brown (00918/2). Old foliage: near Spinach Green (0960/1).

Leaflets:
- *Shape.*—Oval pointed.
- *Texture.*—Upper side—leathery.
- *Edge.*—Serrated.
- *Serration.*—Single, small.
- *Petiole.* — Rachis — Color — Green. Underside — prickles.
- *Stipules.*—Long, serrated.
- *Disease Resistance.*—Partially resistant to mildew under normal growing conditions at Irvine, Calif.

Wood:
- *New Wood.*—Color—Garnet Brown (00918/3). Bark—Smooth.
- *Old Wood.*—Color—Green. Bark—Smooth.

Prickles:
- *Quantity.*—On main stalks from base—ordinary. On laterals from stalk—ordinary.
- *Form.*—Narrow base, long, staight.
- *Color When Young.*—Brown.
- *Position.*—Irregular.

Small Prickles:
- *Quantity.*—On main stalks—few. On laterals—few.
- *Color.*—Brown.

I claim:

1. A new and distinct cultivar of rose plant of the floribunda class, substantially as herein shown and described, characterized particularly as to novelty by the unique combination of an abundantly branched habit of growth, vigorous growth, abundantly doubled flowers of Shrimp Red which are approximately 2½ inches to 3 inches in size when fully opened, having very little fragrance.

No references cited.

ROBERT E. BAGWILL, Primary Examiner

UNITED STATES PATENT AND TRADEMARK OFFICE

CERTIFICATE OF CORRECTION

PATENT NO. : PP 3829

DATED : February 3, 1976

INVENTOR(S) : William A. Warriner

It is certified that error appears in the above-identified patent and that said Letters Patent are hereby corrected as shown below:

Column 2, Line 28, "(6R/2)" should be --(618/2)--

Signed and Sealed this

*eleventh* Day of *May 1976*

[SEAL]

*Attest:*

RUTH C. MASON
*Attesting Officer*

C. MARSHALL DANN
*Commissioner of Patents and Trademarks*